(12) United States Patent
Leschinsky

(10) Patent No.: US 10,213,150 B2
(45) Date of Patent: Feb. 26, 2019

(54) EARLY ALLERGY DETECTION, NOTIFICATION AND MANAGEMENT SYSTEMS AND METHODS

(71) Applicant: Gary A Leschinsky, Mahwah, NJ (US)

(72) Inventor: Gary A Leschinsky, Mahwah, NJ (US)

(*) Notice: Subject to any disclaimer, the term of this patent is extended or adjusted under 35 U.S.C. 154(b) by 200 days.

(21) Appl. No.: 15/224,627

(22) Filed: Jul. 31, 2016

(65) Prior Publication Data

US 2018/0028106 A1 Feb. 1, 2018

(51) Int. Cl.

| | |
|---|---|
| *A61B 5/02* | (2006.01) |
| *A61B 5/00* | (2006.01) |
| *A61B 5/0205* | (2006.01) |
| *A61B 5/103* | (2006.01) |
| *A61B 5/022* | (2006.01) |
| *A61B 5/11* | (2006.01) |
| *G06F 19/00* | (2018.01) |
| *G16H 40/67* | (2018.01) |
| *A61B 5/024* | (2006.01) |
| *A61B 5/053* | (2006.01) |
| *A61B 5/145* | (2006.01) |
| *A61B 5/0245* | (2006.01) |

(52) U.S. Cl.
CPC .............. *A61B 5/411* (2013.01); *A61B 5/002* (2013.01); *A61B 5/0022* (2013.01); *A61B 5/0205* (2013.01); *A61B 5/02233* (2013.01); *A61B 5/1032* (2013.01); *A61B 5/1118* (2013.01); *A61B 5/441* (2013.01); *A61B 5/4839* (2013.01); *A61B 5/681* (2013.01); *A61B 5/746* (2013.01); *G06F 19/00* (2013.01); *G16H 40/67* (2018.01); *A61B 5/0245* (2013.01); *A61B 5/02438* (2013.01); *A61B 5/0533* (2013.01); *A61B 5/1112* (2013.01); *A61B 5/1123* (2013.01); *A61B 5/14517* (2013.01); *A61B 5/14542* (2013.01); *A61B 2560/0242* (2013.01); *A61B 2560/0252* (2013.01); *A61B 2562/029* (2013.01); *A61B 2562/0219* (2013.01)

(58) Field of Classification Search
CPC ....... A61B 5/024; A61B 5/02438; A61B 5/02; A61B 5/411; A61B 5/681
USPC .................................................. 600/503, 556
See application file for complete search history.

(56) References Cited

U.S. PATENT DOCUMENTS

| | | | | |
|---|---|---|---|---|
| 5,897,506 A | * | 4/1999 | Cohn ..................... | A61B 5/411 600/503 |
| 2010/0087744 A1 | * | 4/2010 | Licata ................. | A61B 5/02438 600/503 |

* cited by examiner

*Primary Examiner* — Carl H Layno
*Assistant Examiner* — Jon Eric C Morales
(74) *Attorney, Agent, or Firm* — Boris Leschinsky

(57) ABSTRACT

A watch-like early allergy detection, notification and management system is equipped with a motion detector as well as one or more physiological sensors to measure heart rate, skin color change, skin galvanic response, oxygen saturation and blood pressure to detect early symptoms of an allergic reaction. False alarms are reduced by simultaneously measuring ambient temperature and physical activity of the subject. Sudden onset of skin itch, redness, sweating, increase in heart rate or a drop in blood pressure without a preceding hot ambient condition or strenuous physical activity is interpreted as an allergic reaction. The system is also equipped with a subject locator and a GPS receiver to assist a caregiver in finding the subject rapidly. The system further features a medication compartment to start managing the allergic reaction quickly. The system is particularly beneficial for children that may become scared or hide away upon onset of an allergic reaction.

19 Claims, 8 Drawing Sheets

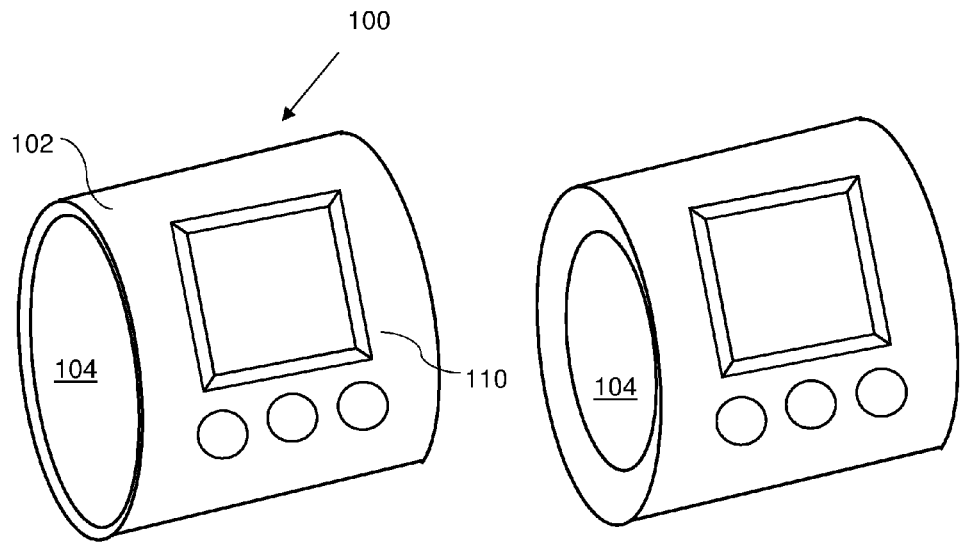
FIG. 4  FIG. 5
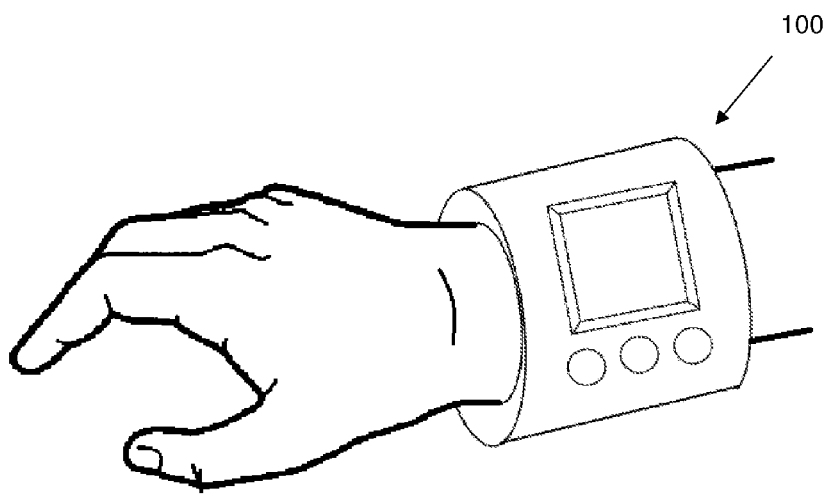
FIG. 6

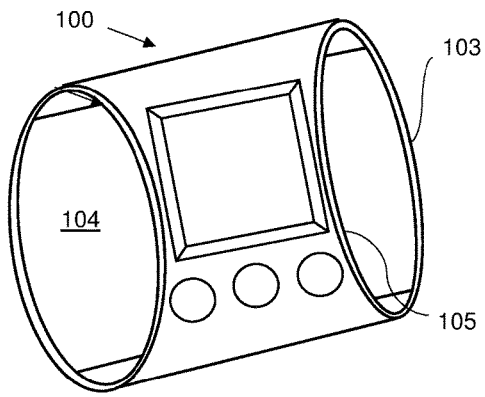 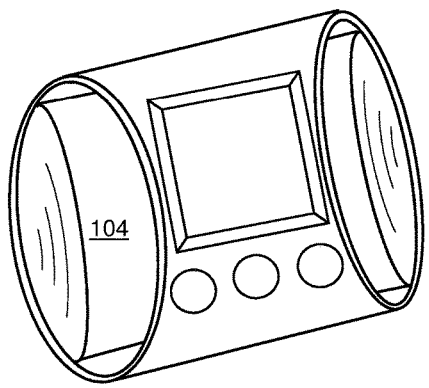
FIG. 7  FIG. 8
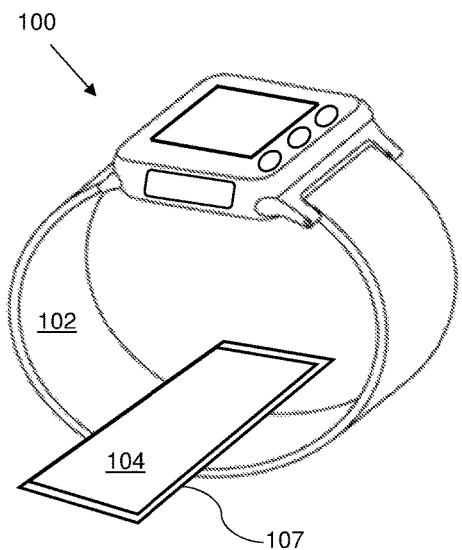 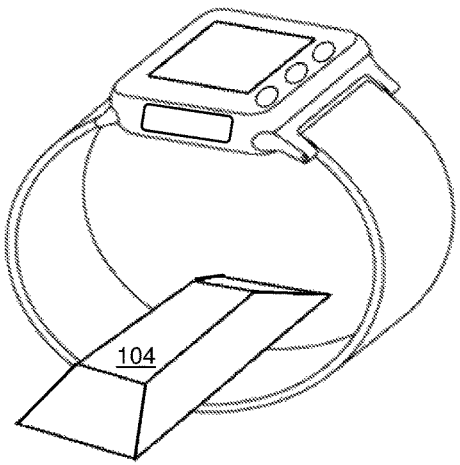
FIG. 9  FIG. 10

EARLY ALLERGY DETECTION, NOTIFICATION AND MANAGEMENT SYSTEMS AND METHODS

BACKGROUND

The present invention relates generally to wearable sensor systems. More particularly, the invention describes a watch equipped with a series of physiological sensors configured to detect early symptoms of an allergic reaction.

About 50 million Americans have one or more allergies, with as many as 15 million having some form of food allergy. That number includes about 6 million or 8% of all children, with young children affected most. According to a study released in 2013 by the Centers for Disease Control and Prevention, food allergies among children increased by approximately 50% between 1997 and 2011. Every 3 minutes, a food allergy reaction sends someone to an emergency department—that is more than 200,000 ER visits per year. Food allergies cause an estimated $25 billion burden on the US economy every year.

Young children are not only more likely to have food allergies, they are more vulnerable to suffer greater consequences from them. This is in part due to the fact that children are less likely than adults to recognize foods that they may be allergic to. Children are also less likely to recognize early symptoms of an allergic reaction and less likely to take quick steps to manage its consequences. Novel systems and methods are therefore needed to help adults with objective recognition and notification of an onset of an allergic reaction of their child.

Another component of the problem is that an allergic reaction may not start immediately after digesting the culprit food. It may take some minutes and even hours for some allergic reactions to develop. Small children may not be easy to continuously monitor and observe. They can wonder away from adults to play in other rooms in the house or hide in a closet somewhere, thereby further complicating the task of direct monitoring of their condition by an adult. There is a need for a novel system capable of not only recognizing the early onset of an allergic reaction but also capable of assisting an adult in rapidly finding a child that needs medical attention.

Food allergy occurs when a person's immune system mistakenly treats a specific food as an invading disease, releasing histamine into a blood stream. In turn, histamine release may cause a variety of physiological reactions ranging from swelling, skin itching, hives and irritation, to excessive sweating, increase in heart rate, drop in blood pressure and even airways restriction and anaphylaxis. Frequently, the person experiencing an allergic reaction may not even realize it until the process has gone too far.

Unfortunately, early signs and symptoms of an allergic reaction are too ubiquitous to be of specific value in allergy detection. Skin redness and sweating may be caused by common environmental factors such as hot ambient temperature and high humidity or by strenuous physical activity such as running, biking or jumping—something that children often do many times a day. Monitoring for allergy may therefore be a subject of frequent false alarms, which may frustrate their caregiver to the point of making such devices useless. There is a need for a system capable of accurate detection of an onset of an allergic reaction with minimal false alarms.

Finally, early detection and notification of an allergic reaction is not useful unless it is accompanied by a rapid mitigation strategy, such as intake of an antihistamine medication or injection of epinephrine. Since such allergic attacks may not be occurring frequently, locating suitable medication may prove to be difficult and may take some time, thereby worsening the outcome. Novel systems and methods are therefore needed that will assist a caregiver with rapid location of the necessary medication so that this medication may be administered as soon as possible.

SUMMARY

Accordingly, it is an object of the present invention to overcome these drawbacks by providing a novel watch-like devices and methods configured to be positioned on a subject's wrist and equipped with sensors to detect ambient conditions, physical activity and signs of allergic reaction.

It is another object of the present invention to provide an early allergy detection systems and methods designed to minimize false alarms, such systems including a watch with a controller operably connected with a plurality of sensors and configured to distinguish an early allergic reaction from normal physiological changes triggered by a change in environment or excessive physical activity.

It is a further object of the present invention to provide a novel early allergy detection and notification system including a watch equipped with a plurality of sensors and a subject locator so as to assist a caregiver in locating the subject.

It is yet a further object of the present invention to provide a novel early allergy detection and management system including a watch with a plurality of sensors and a medication storage compartment so as to expedite the beginning of allergy treatment steps.

The system of the invention comprises a first watch featuring a controller connected to a number of sensors providing data on ambient conditions, physical activity of the subject, skin condition of the subject and optionally other physiological measurements such as blood pressure and oxygen saturation. The first watch may further include a subject locator and a medication storage compartment. The watch may be configured to generate a local alarm and/or send a wireless notification to a caregiver in the event of detecting an early allergic reaction.

To minimize false alarms, the methods of the invention may include steps of collecting physiological data from one or more physiological sensors to detect a possible symptom of an allergic reaction. Ambient and physical activity data may then be analyzed for a preceding predetermined period of time to determine if such symptom may have been caused by hot and humid ambient conditions or by strenuous physical activity, in which case the symptom may be ignored. If none of such ambient or physical activity conditions were present, a local or wireless alarm may be activated to alert a caregiver to a possible onset of an allergic reaction.

In embodiments, a second watch and/or further skin sensors may also be provided to form a more comprehensive system to detect additional signs of an allergic reaction, all devices may be configured to communicate with a first controller of the first watch.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 4 is a general view of the early allergy detection watch configured to measure blood pressure—with an inflatable cuff shown in deflated state;

FIG. 5 is the same as in FIG. 4 but showing the inflatable cuff in its inflated state;

FIG. 6 shows the device of FIG. 4 on a wrist of the subject;

FIG. 7 shows an alternative design of the watch of FIG. 4 with the inflatable cuff in deflated state;

FIG. 8 shows the same as FIG. 7 but the inflatable cuff is shown in its inflated state;

FIG. 9 shows yet another alternative design of the watch of FIG. 4 with the inflatable cuff in its deflated state;

FIG. 10 shows the same as FIG. 9 but the inflatable cuff is shown in its inflated state;

DETAILED DESCRIPTION OF THE PREFERRED EMBODIMENT OF THE INVENTION

Figure 1:
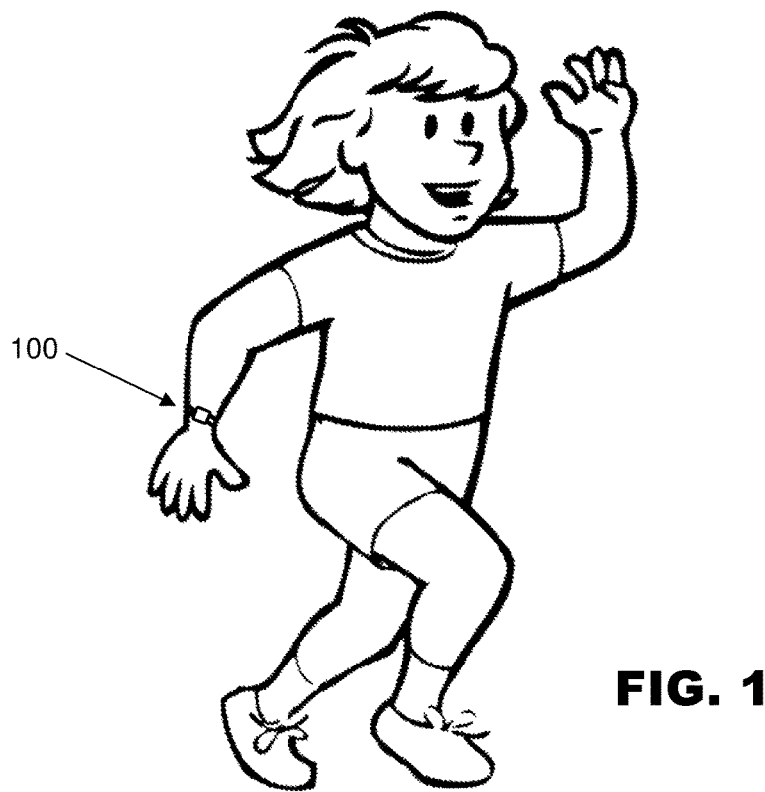
FIG. 1 is a general view of a subject wearing the early allergy detection and notification watch of the present invention.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

FIG. 1 shows a general view of the device 100 of the present invention made to be perceived as a watch on a subject's wrist. The present invention may also be made to look like a bracelet, a bangle or a strap, as the invention is not limited in this regard.

Figure 2:
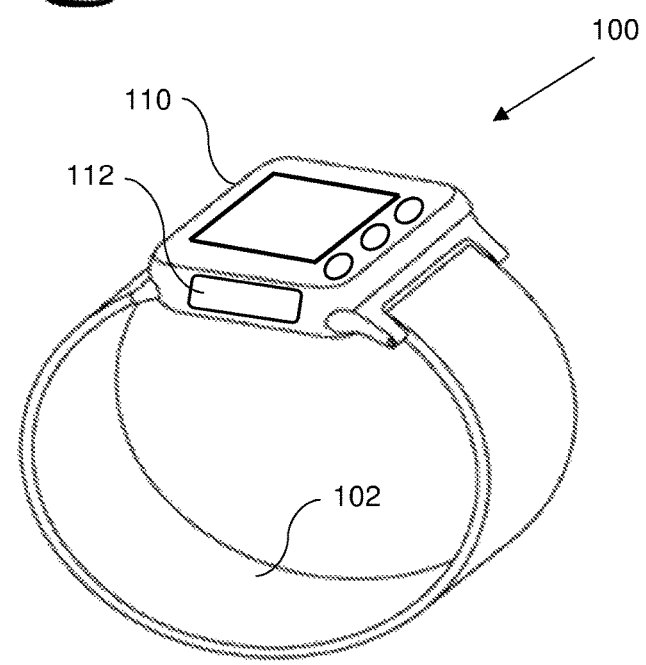
FIG. 2 is a general view of the early allergy detection watch of the invention.

FIG. 2 shows a closer view of the device 100 of the present invention. It generally includes a first watch 110 attached to a wristband 102. In embodiments, the wristband 102 may be made as a generic flexible watchband made to be expandable or with a conventional clasp, as the invention is not limited in this regard. In other embodiments, the wristband 102 may include some elements of the watch, such as sensors or an inflatable cuff and therefore the wristband 102 may form an integral part of the device 100 of the invention.

Figure 3:
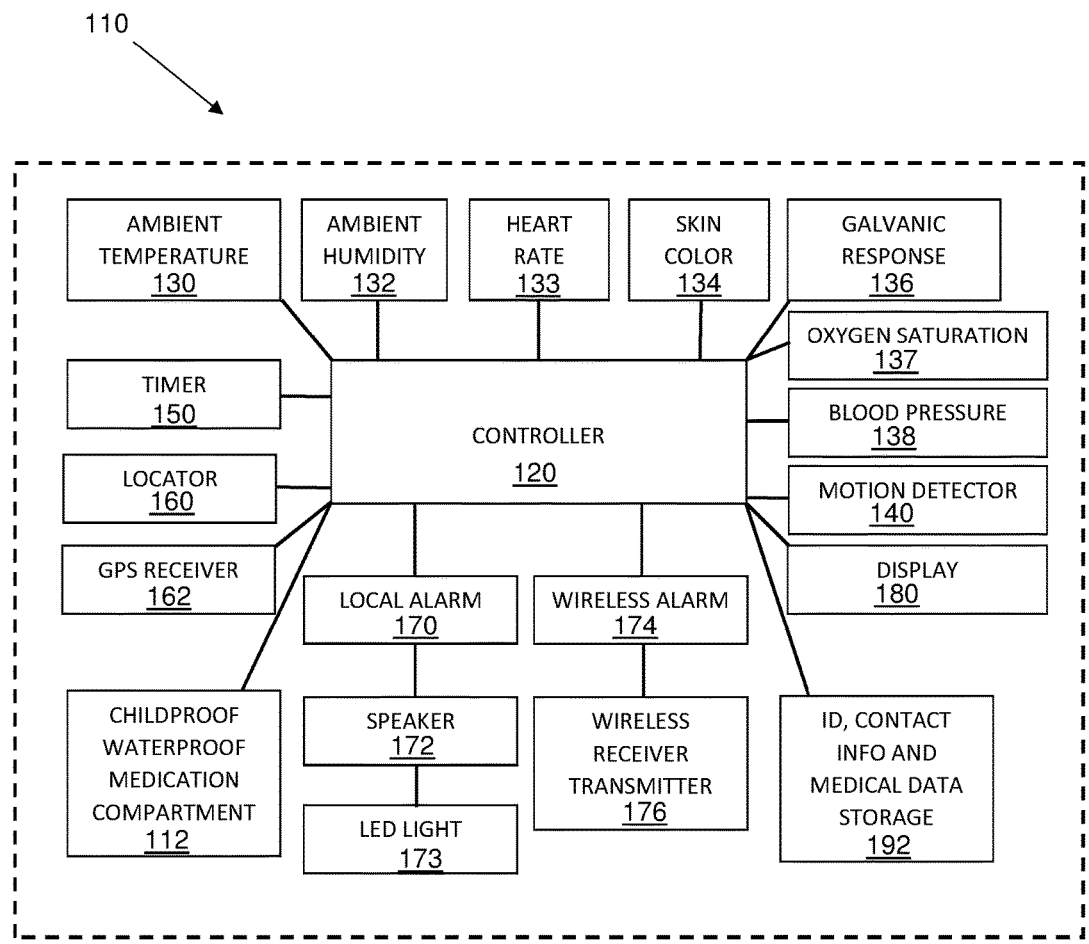
FIG. 3 is a block-diagram of the early allergy detection watch of the invention.

FIG. 3 depicts a block-diagram of the first watch 110 comprising a first controller 120 operably connected to a plurality of sensors and other components described below in greater detail. The first controller 120 may include a programmable microprocessor powered by a battery or another portable source of electricity, such as a solar energy cell. The microprocessor may in turn comprise any suitable programmable computing device or integrated circuit board capable of operating the sensors and other elements of the watch 110 in a manner described below. The first controller 120 may also include a computer memory element and control buttons suitable for operating the device 100 of the invention.

A watch timer 150 may be either operably connected to or its function may be integrated with the first controller 120. The watch timer 150 may be used to show time, date and other data as needed, such as setting an alarm, working as a stop-watch, etc. on a display 180.

Ambient Monitoring

The first watch 110 may include one or more sensors to monitor ambient environment. Such sensors may include an ambient temperature sensor 130 and/or an ambient humidity sensor 132. Data from ambient sensors 130 and 132 may be transmitted continuously or from time to time to the first controller 120 and used to differentiate a skin response to an early allergic reaction from a changing skin state caused by a change in ambient conditions as described in more detail below. In order to improve the accuracy of the early detection of an allergic reaction, a periodic update of environmental ambient conditions may be transmitted to the first controller every 1 min, 2 min, 3 min, 5 min, 10 min, 15 min, 20 min, 30 min, 60 min, 90 min, or 120 min.

Physical Activity Monitoring

Physical activity monitoring may be performed using a motion detector 140 as described in greater detail below.

Physiological Monitoring

Non-invasive physiological monitoring of the subject and in particular the skin of the subject may be conducted on a continuous or periodic basis by one or more physiological sensors described below in greater detail. In at least some embodiments, a heart rate monitor 133 may be provided as part of the watch 110, which may include one or more dedicated skin electrodes located on an inner surface of the watch 110 or the wristband 102. In other embodiments, electrodes on the inner surface of the watch 110 from other sensors as described below may also be used for the purpose of detecting heart rate. Electrical activity of the subject may be detected on a continuous or intermittent basis and used to extract the heart rate data. Examples of known wrist-worn heart rate detectors suitable for the purposes of the present invention may be found in the U.S. Pat. No. 4,938,228 or US Patent Application No. 20130178753, both incorporated herein by reference in their respective entireties by reference. The present invention may use the same or similar approach in detecting a change in heart rate, which for the purposes of this invention may be used as an indication of an onset of allergic reaction. Heart rate may also be detected using other approaches such as plethysmography and blood pressure monitoring, as described in greater detail below.

Onset of allergic reaction may cause skin color to change to red and rash to appear. It may be useful to monitor skin color as at least one indicator of an allergic reaction. In at least some embodiments, the first watch 110 of the invention may include a skin color sensor 134 such as for example an inward-looking small camera directed at the area of skin under the watch 110 or in close proximity to the watch 110 in order to observe skin appearance and detect any change in skin color towards redness.

Sweating is another common symptom of an allergic reaction. Detection of onset of sweating may be a useful tool in recognizing an early onset of an allergic reaction. Skin galvanic response sensor 136 may be incorporated into the watch 110 in at least some embodiments in order to detect sweating. Galvanic response sensor 136 may include two, three or more skin electrodes located on the inner surface of the watch 110 and/or the wristband 102, such electrodes may be configured to measure electrical conductance or impedance of the skin inbetween thereof. Sweating lowers electrical resistance of skin considerably and so monitoring for a change in electrical resistance may be used to detect sweating. Skin-contacting electrodes of the heart rate sensor 133 and the galvanic response sensor 136 may be the same in some embodiments, while in other embodiments each sensor may have its own dedicated set of electrodes. Still in further embodiments, at least some electrodes may be shared between the two sensors 133 and 136.

Breathing may become impaired as a result of a severe allergic reaction. Anaphylaxis may cause significant narrowing of breathing passages and reduce oxygen available for circulation. Monitoring of oxygen level in blood may be used at least in some embodiments of the present invention as a method for detecting severe breathing anomaly, which may be indicative of an allergic reaction. Oxygen saturation sensor 137 may be included in the first watch 110 and may have an optical sensor configured for performing a plethysmography. One suitable sensor of this type is described in greater detail in the WO 2015/157712 which is incorporated herein in its entirety by reference.

Another physiological parameter that may change as a result of ongoing allergic reaction is blood pressure. At least some embodiments of the present invention may include a wrist-worn blood pressure sensor. Wrist sphygmomanometers are generally known in the art, as seen for example in the U.S. Pat. No. 6,547,741 incorporated herein by reference in its entirety. They generally include an inflatable cuff attached to a pneumatic assembly containing an air-pump, one or two valves, and a pressure sensor. When such elements are incorporated into the first watch 110, they may be operably connected to the first controller 120, which may be configured in this case to support and control their operation.

Inflation of the cuff is used for brief arterial occlusion. Slow continuous or stepped deflation gradually releases such occlusion—blood pressure may then be determined using an oscillometric technique. To measure the blood pressure with sufficient accuracy, inflatable cuff needs to be wider than a traditional wrist band. In embodiments, as shown in FIG. 4 the wristband of the watch 110 may be made to be wider than shown for previous embodiments so that the inflatable cuff 104 (shown in a deflated state) may be incorporated therewith on its inner surface. Inflation of the cuff 104 (shown in FIG. 5) temporarily compresses the tissues of the wrist including the radial and ulnar arteries for the purposes of measuring subject's blood pressure. In embodiments, the band 102 may be made rigid so as to act as a back stop for the inflatable cuff 104 directing it to move inwards and compress the wrist. In other embodiments, the inflatable cuff may not be configured to inflate concentrically within the band 102. It may be configured to inflate to a greater extent near the portion of the band opposite the first watch 110, and correspondingly inflate to a minimum extent or not at all in the areas directly underneath or adjacent to the internal surface of the watch 110, as seen in FIG. 5. This may be advantageous so as not to disrupt continuous skin contact of the internal surface of the watch 110 with all of its other sensors, which in case of such disruption may make them inoperable.

To minimize the use of electrical power and to reduce the size of batteries in some embodiments, the first controller 120 may be programmed to initiate a blood pressure measurement only if a detection of a possible allergic reaction has been recorded by other sensors of the first watch 110.

In embodiments, it may not be necessary to accurately detect systolic and diastolic blood pressure of the subject. Instead, it may be sufficient to make sure the subject does not have blood pressure below a safe predetermined threshold. One measure of such predetermined threshold may be a mean arterial blood pressure not dropping below a predetermined limit such as for example 50 mmHg, 60 mmHg, 70 mmHg, 80 mmHg, 90 mmHg or any number inbetween. Detection of a mean arterial pressure may be done by detecting a peak in an oscillometric amplitude. To minimize the power requirement for operating a blood pressure sensor of the present invention, the first controller 120 may be configured to only pressurize the inflatable cuff 104 to a predetermined safe level of mean blood pressure or slightly above that level, for example 5, 10, or 15 mmHg above. If no peak in oscillometric amplitude is detected but oscillometric pulses have been recorded with increasing amplitudes, a conclusion may be made that the subject is not having a condition of low blood pressure, although the actual blood pressure measurement has not been actually performed. The inflatable cuff 104 may then be deflated immediately. In further embodiments, the inflatable cuff 104 may be deflated slowly and in predetermined steps of dropping cuff pressure by 3-5 mmHg at a time in order to record amplitudes of oscillometric pulsations on the way down. That may confirm again that the mean arterial pressure is above the predetermined safe threshold.

Other measurements of blood pressure may be used to determine whether the blood pressure of the subject is above the minimum safe level. One such measure may be a diastolic blood pressure. In embodiments, the minimum safe level for diastolic blood pressure may be set at 40, 45, 50, 55, 60, 65, 70, 75, 80 mmHg or any number inbetween. Another measure of blood pressure may be a systolic blood pressure. In embodiments, a minimal safe level of systolic blood pressure may be set at 70, 75, 80, 85, 90, 95 mmHg or any number inbetween.

FIG. 6 shows the device 100 seen in FIG. 4 in use over a wrist of the subject. In embodiments, instead of deflating the inflatable cuff 104 completely, the first controller 120 may be configured to keep a small retaining level of air pressure in the cuff 104 such as about 5, 10, 15, 20, or 25 mmHg in order to retain the device 100 snugly over the wrist of the subject and to assure that all skin sensors and electrodes are staying on close contact with the skin of the subject. In addition, the device 100 may be prevented in this case from freely rotating around the wrist of the subject.

In further embodiments, the inflatable cuff 104 may be also used to periodically detect heart rate of the subject, in which case there may not be a need for a dedicated heart rate sensor 133. Heart rate may be detected from analyzing the rate of pulsatility of oscillometric amplitudes recorded by the pressure sensor of the blood pressure measurement assembly 138.

In further embodiments, the device 100 featuring a wrist blood pressure sensor 138 may be made having a band 102 with a sufficiently wide inner wrist section 103 containing the inflatable cuff 104 and a narrow outer wrist portion 105 adjacent the first watch 110. FIG. 7 shows one example of such device with the inflatable cuff 104 shown in deflated state. FIG. 8 shows the same with the inflatable cuff 104 shown in inflated state. The width of the section 103 may be 2 or 3 times larger than the width of the section 105.

A further variation of that design approach is seen in FIGS. 9 and 10. In this embodiment, the wider inflatable cuff 104 is designed to work with a wristband 102 of conventional width, so as to further minimize the size of the device 100. In this embodiment, there is provided a rigid support plate 107 sized to match the size and shape of the inflatable cuff 104, which is located on the inner surface of the support plate 107. FIG. 9 shows the inflatable cuff 104 in a deflated state, while FIG. 10 shows the same with the inflatable cuff 104 in an inflated state. The presence of the support plate 107 causes the inflatable cuff to inflate inwards so as to compress the wrist tissues and arteries upon inflation. The size and shape of the inflatable cuff or bladder may be selected to adequately compress the ulnar and radial arteries of the wrist for the purposes of detecting blood pressure of the subject.

Motion detector 140 may be included in a set of sensors of the first watch 110. Such motion detector may include one or multiple one-dimension, two-dimension, or three-dimension accelerometers, position sensors or gyroscopes. The signal from the motion sensor 140 may be used for two different purposes:
  (i) detection of the overall gross movements of the subject's body, such as walking, running, jumping, biking, etc, which may be indicative of a level of physical activity of the subject, and
  (ii) detection of periodic limb movements of the subject for extracting signal features indicating persistent scratching of the subject's skin, which may be a symptom of an onset of an allergic reaction.

For the purposes of determination of physical activity of the subject via gross movements, the motion detector 140 of the present invention may be configured to detect the number and frequency of steps using known techniques described for example in the US Patent Applications Nos. 20160058336, 20160058337, and 20070054778, all incorporated herein in their respective entireties by reference. Such techniques may be used to separate strenuous physical activity from normal body movements so as to identify possible non-allergic reasons for skin sweating, heart rate increase or skin redness as will be described below in greater detail.

Figure 11:
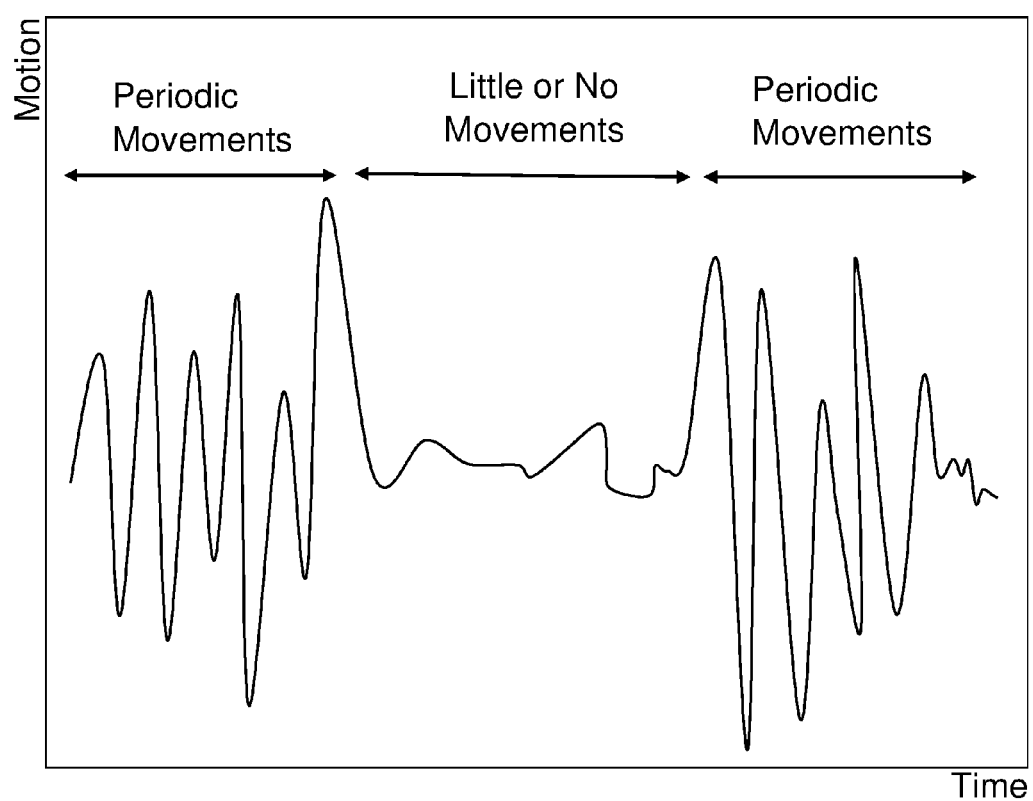
FIG. 11 shows an exemplary tracing of the motion detector.

Periodic limb movement detection using the same motion detector 140 may be used to detect whether a subject has a skin itch urging periodic scratching on the skin. The onset of itching and corresponding scratching of the skin may be determined if a pattern of new periodic limb movements is detected that are repeated a predetermined minimum number of times with a predetermined interval of time with no limb movement or random limb movements inbetween. FIG. 11 shows an exemplary motion vs. time chart in which a first series of 6 periodic movements is followed by a period of little or no movements and then again by a series of another 5 periodic movements. To accurately define the presence of persistent skin scratching, the following one or more conditions may need to be met:
  a. Each series of periodic movements includes between about 3 to about 20 of such movements;
  b. There is at least 3 or more of such series of periodic movements present over a period of 1, 2, 3, 4, 5, 6, 7, 8, 9, 10, 15, 20, or 30 min;
  c. Each of these series of periodic movements is separated from another series by a period of no, little or random limb movements lasting about 1, 2, 3, 4, 5, 6, 7, 8, 9, 10, 15, or 20 min;
  d. The amplitude of such periodic movements is in a range from about 0.5 inch to about 5 inch;
  e. The watch spatial orientation in at least some or more of such series of periodic movements is about the same or substantially the same indicating scratching of the same portion of skin with the same limb posture;
  f. The frequency of the periodic motions is about the same (within 20%) between successive series of periodic movements;
  g. The frequency of periodic movements in each series is in a range from about 40 times per minute to about 150 times per minute.

A confidence score may be developed to assess the accuracy of itch detection based on how many of the preceding conditions are met—the more conditions that are met, the higher is the confidence score of detecting an onset of a new skin itch or rash. For example, if 4 or more out of 7 measures as described above are met, detection of itch may be confirmed with high degree of accuracy. In further embodiments, each of the above measures may be assigned a certain weight so that the final score may be generated using individual importance of each of these measures.

The use of 3-D accelerometers may be advantageous over a single-dimension accelerometer because spatial orientation of the watch during a suspected series of periodic movements may be assessed with greater accuracy. Repeated periodic movements of the limb with the watch in the same spatial orientation may indicate repeated scratching of the skin in the same place by the subject.

Onset of an allergic reaction may trigger an urge to scratch simultaneously at more than one skin portion. In this case, two or more series of periodic movements may overlap each other making motion analysis more complicated. 3-D accelerometers may be particularly useful in this case as they may allow to separate repeated motion of the watch 110 for different planes of spatial orientation.

Early Allergy Notification System

Referring again to FIG. 3, the early allergy notification system of the first watch 110 may be configured to serve as a personal identification, medical data storage, and medical alert bracelet. The first controller 120 may be configured to cause the display 180 to show the name, contact info and basic medical alert information upon triggering an alarm of a possible allergic reaction. In other embodiments, such information may be read out loud (once or repeatedly) using a computer-generated voice or by playing a prerecorded customized message through a speaker 172 of the watch 110.

In case of a child subject, this may be particularly useful for rapidly contacting child's parents or guardians if the child is away from home, for example in a child care facility. An example of a medical data stored by the watch 110 and displayed in an allergic alarm situation may include a message "ALLERGY TO PEANUTS" or another specific message describing a particular allergy of the subject. The first controller 120 may be configured to allow entry, storage, and editing of personal information about a particular subject.

Upon detecting an alarm condition using methods described below in greater detail, the first watch 110 may be configured to generate a local and/or wireless alarm. For that purpose, a wireless alarm 174 may include a wireless receiver/transmitter 176, which may be configured to operate using common wireless protocols such as for example cellular, Bluetooth or WiFi. In case of transmitting to the cloud, suitable log-in and communication protocols may be established to continuously connect the first watch 110 to the Internet. Examples of wireless notifications may include predetermined messages to parents, caregivers, medical personnel, or guardians of the subject.

Local alarm 170 may also be provided as part of the first watch 110. Local alarm 170 may be a visual alarm and/or an audible alarm. A visual alarm may be realized as a flashing alarm message using a display 180. Visual alarm may also be realized using a dedicated LED light 173, which may be incorporated into a housing of the first watch 110. This is particularly advantageous as the flashing LED light 173 may be designed to be much brighter than a flashing alarm message on the display 180. An audible alarm may be activated using the watch speaker 172 and may include a series of loud beeps or a prerecorded message, which may be activated once or on a repeated basis.

Early Allergy Management System

Once the early allergy alert conditions are met and an alarm notification is sent, the first watch 110 may be further configured to assist in managing and mitigating the allergic reaction of a subject. The watch 110 may comprise a locator 160, which may be helpful in rapidly finding the subject by a caregiver. The locator 160 may be a wireless beacon configured to generate a homing signal that can be detected by a suitable hand-held homing device or a wireless grid system such as for example those deployed in a hospital. As time is of the essence, the use of a locator 160 may advantageously expedite finding the subject to start allergic treatment immediately.

In embodiments, the locator 160 may be supplemented with a GPS receiver 162 configured to detect the coordinates of the subject. Such coordinates may be transmitted as part of a wireless notification alert message via the wireless alarm 174.

GPS coordinates may also be transmitted to a caregiver or a parent's smart phone wirelessly over the Internet from time to time or continuously so as to allow the watch 110 to serve in a secondary function as a child location device.

The locator 160 may have a particularly advantageous utility for a child subject. A child with an allergic reaction may become scared and unable to call for help. In addition, the child may hide in a closet or under the table somewhere, which may make it difficult for a parent or a caregiver to rapidly find the child and initiate treatment steps.

Figure 12:
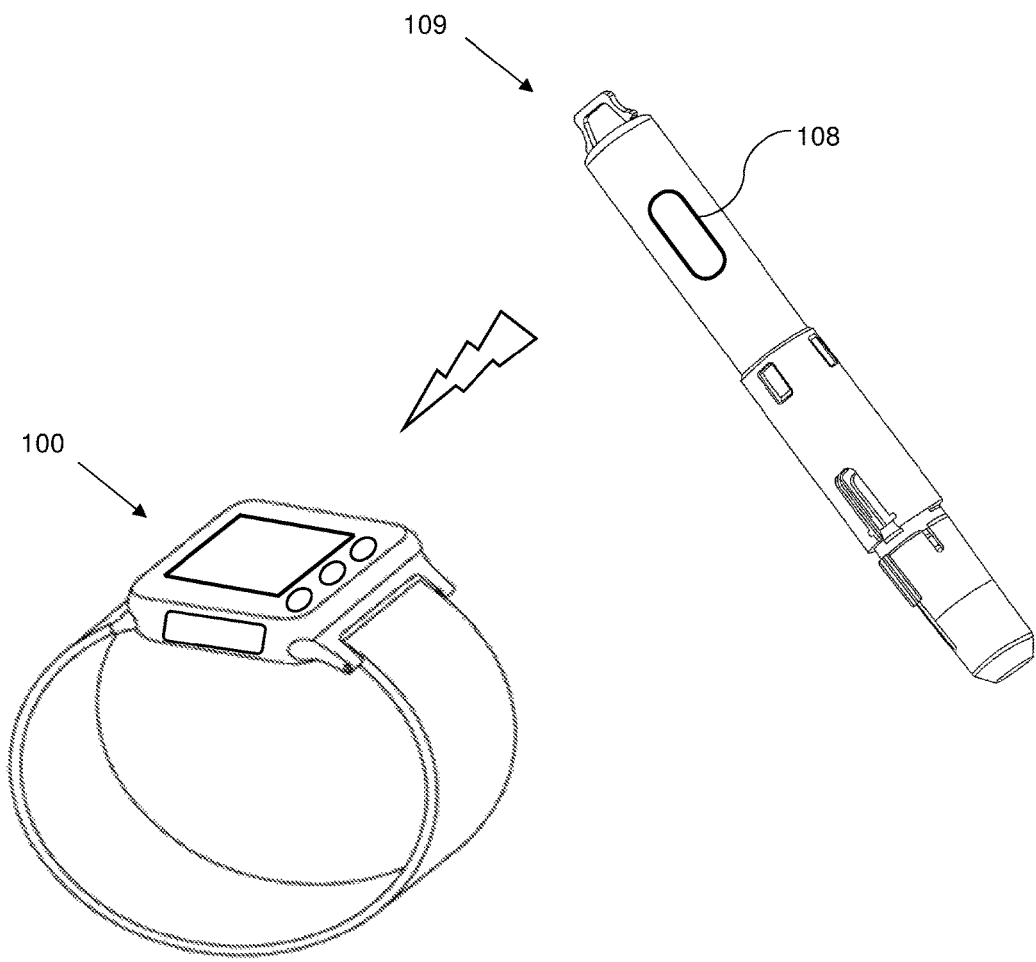
FIG. 12 shows a first watch communicating via a wireless locator with a beacon affixed to an injector of suitable medication.

One of the most potent ways to reduce the effects of an allergic reaction is to inject a medication such as epinephrine. Allergy patients are advised to keep such injector nearby. Since allergy attacks may happen infrequently, a subject or a caregiver for a subject may forget where such injector is stored. Looking for an epinephrine injector may take some time and delay the treatment procedure. In case of a severe allergy attack, any delay may increase the risk of suffocation and even death. Assistance in rapidly locating a medication injector may prove very beneficial in such situations. The locator 160 may be further configured to communicate wirelessly with a beacon 108, which may in turn be affixed to a medication injector 109 containing epinephrine or another suitable injectable medication for treating allergy—see FIG. 12. The beacon 108 may also be affixed to a first aid kit or another item needed for management of an allergic reaction of the subject. In embodiments, more than one beacon 108 may be provided to assure rapid access to all items needed for treating an allergy.

In embodiments, the beacon 108 may be activated by a locator 160 via a wireless signal transmission generated for example by the wireless receiver/transmitter 176. Once activated, the beacon 108 may be configured to produce visual and/or audio signals or beeps that may help a caregiver to identify the location of the medication injector 109. In other embodiments, activated beacon 108 may be configured to produce a homing radio signal that can be received by the first watch 110 and transformed into a communication on a display indicating a direction towards the beacon 108.

Another method of treating allergy is with a pill of a suitable antihistamine medication, such as Benadryl™. Locating that pill quickly may be advantageous in expediting treatment steps and managing the allergic attack. The watch 110 may be equipped with a medication storage compartment 112, which may contain a first dose of a suitable medication. This storage compartment may be made waterproof so that the pill remains viable over a long period of time. In addition, the medication storage compartment may be made childproof so that a child subject cannot open the compartment to reach the pill and ingest it inadvertently. In embodiments, the medication storage compartment 112 may be designed with an electronically-locked trap door, which may be opened electronically only in case when an allergy alert conditions are present. In other embodiments, the trap door may be unlocked by entering a code or a password into the watch 110.

Second Watch

To further improve the performance of the early allergy detection system of the present invention, it may be advantageous to increase the extent of monitoring of the subject with more sensors located at other parts of the body. For example, in case of an onset of skin itch, the subject may scratch the itching portions of the skin with an arm other than that which contains the first watch 110. In other situations, skin redness or rash may appear in places other than the vicinity of the device 100. To compensate for such situations, a second watch 200 may be provided as part of the system of the present invention—see FIG. 13. Such second watch 200 may be identical in design to the first watch 110—in which case the first controller 120 may be programmed to cause the first watch device 100 to serve as a primary watch. The second watch 200 may be configured to serve as a secondary data collection instrument—communicating data from its sensors wirelessly to the first controller 120.

Figure 14:
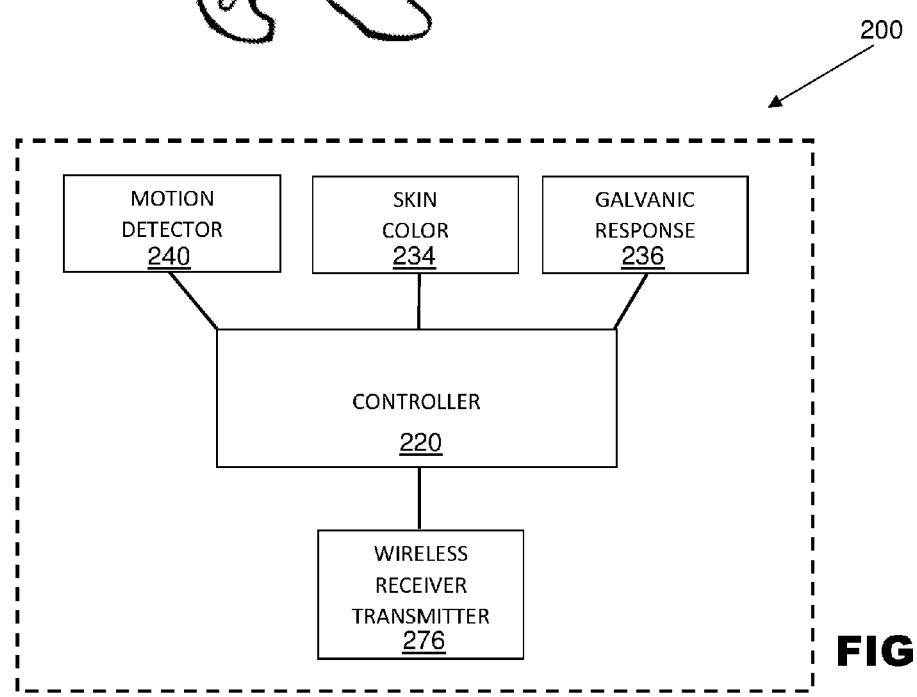
FIG. 14 contains a block-diagram of the second watch of the invention.
Figure 15:
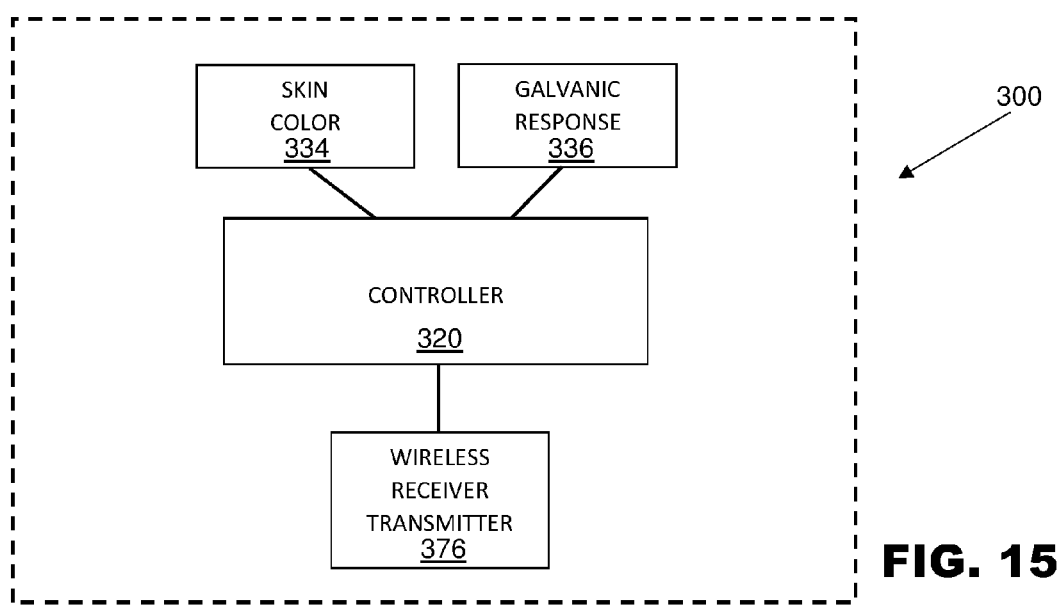
FIG. 15 shows a block-diagram of additional skin sensors of the invention.

In other embodiments, the design of the second watch 200 may be simplified as compared with the first watch 110—see a block-diagram of the second watch 200 shown in FIG. 14. In this case, the second battery-powered controller 220 may be operably connected only with a second wireless receiver/transmitter 276 and at least one of a second motion detector 240, second skin color sensor 234, and second galvanic response sensor 236. Designs of all such sensors may be similar or the same as the corresponding sensors described above for the first watch 110. A set of one or more of the second sensors may be used to collect additional data and therefore improve the recognition accuracy of a true allergic reaction from other situations—as described in greater detail below.

Additional Skin Sensors

Figure 13:
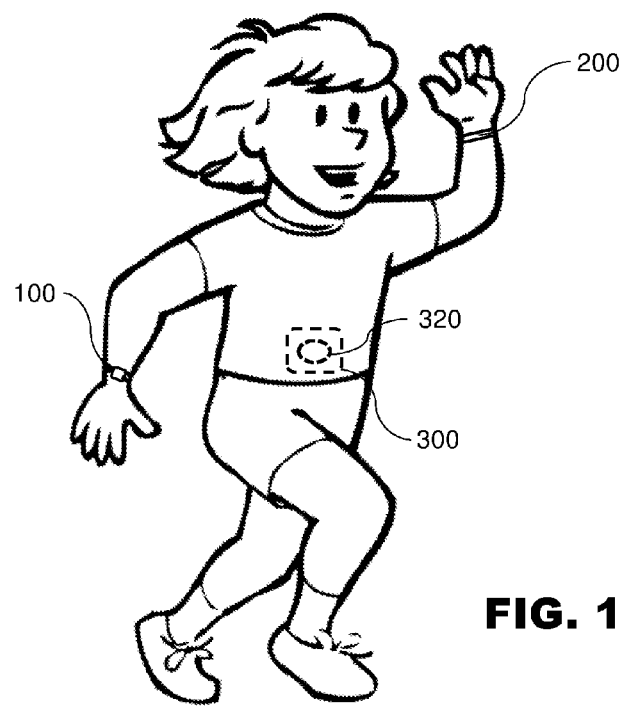
FIG. 13 shows an expanded system of the invention in use on a subject featuring a first watch, a second watch and additional skin sensors.

In embodiments, additional one or more skin sensors 300 may be provided to further increase data collection and physiological monitoring of the subject—see FIG. 13. Each additional skin sensor 300 may include a third battery-powered controller 320 operably connected to at least one of the skin color sensor 334 and/or skin galvanic response sensor 336. Communication with the first controller 120 for sensor data transmission may be made using a wireless receiver/transmitter 376. Additional skin sensors 300 may be affixed to areas of skin known to become red or develop a rash in case of an allergic reaction, such as an abdomen, back or other areas specific for each subject. Skin sensor 300 may be retained in contact with a skin using an adhesive layer, a tape, a belt, a clip, an elastic band, a strap or other suitable means. Skin sensor 300 may also be attached inside to a piece of tight clothing, which may then be used to retain the skin sensor 300 against the skin of the subject.

Early Recognition of Allergy Onset

The operation of the early allergy detection, notification and management system of the present invention will now be described in greater detail.

Although the watch of the invention may be equipped with sufficient number of sensors to detect a variety of common symptoms of an allergic reaction, all of these symptoms may also occur in situations other then an allergic reaction. For example sweating and skin redness may also occur in a hot and humid ambient climate or as a result of strenuous physical activity. Therefore, the first watch 110 may be programmed in addition to physiological monitoring to monitor ambient conditions and the extent of physical activity of the subject.

Continuous data streams or periodic measurements from all sensors may be recorded and retained for a predetermined period to time, such as the preceding 5 min, 10 min, 15 min, 20 min, 30 min, 45 min, 60 min, 90 min, 120 min, 150 min, or 180 min. When physiological monitoring indicates one or more of conditions of a possible allergic reaction, the first controller 120 may be programmed to perform "a look back" into ambient conditions and a history of physical activity over the preceding predetermined period of time prior to a time when a possible allergic reaction has been detected. This may be done to determine if allergic symptoms may have been caused by reasons other than an allergic reaction.

The first controller may be configured to recognize "normal" and "elevated" state for each measurement provided by the sensors of the system. The elevated state may be designated using a relative or an absolute predetermined threshold for each respective measurement as outlined in one example below:

a. Ambient temperature—above about 75 degrees F.;
  b. Ambient humidity—above about 75 percent;
  c. Physical activity via motion detector—walking, running, biking, or jumping with a rate exceeding about 100 steps per minute;
  d. Heart rate—above about 110 beats per minute;
  e. Skin color—shift towards red by at least about 30 percent of red wavelengths and hue;
  f. Galvanic response—increase in skin conductance by at least about 30 percent;
  g. Oxygen saturation—reduction to about 93 percent or below;
  h. Blood pressure—drop of mean arterial pressure below about 70 mmHg;
  i. Itch detection—using a confidence score or meeting individual conditions described above.

The method of operating the first controller for the system of the invention may include the following steps:

1. Collect ambient data, physical activity data and physiological data for the sensors of the first watch 110 as well as additional sensors of the second watch 200, additional one or more skin sensors 300 if available;
2. Monitor physiological data to exceed respective predetermined thresholds indicating a change from a normal state to an elevated state for at least one or more of the physiological sensors;
3. Upon detection of an elevated state for at least one physiological sensor, analyze ambient and physical activity data for the preceding predetermined period of time, for example for the preceding 15 min;
4. If at least one or more of ambient or physical activity sensors were recorded in their respective elevated states, ignore the elevated state of the physiological sensor, which is likely a result of circumstances other than an allergic reaction;
5. If no ambient or physical activity sensors were in their respective elevated state during the preceding period of time, activate allergy alert notification system to indicate a possible early onset of an allergic reaction.

The system of the present invention may further be configured to adjust and personalize predetermined or preset thresholds for various sensors using a display 180 or via connecting the watch 110 wirelessly or via a cable to a computer, a tablet, or a smartphone. A suitable user interface program may be provided to allow the user to vary the thresholds of the sensors, enter subject ID, contact data, and medical information and retrieve prior alarm notifications.

The system of the present invention may be further configured to improve the accuracy of detecting an allergic reaction over time by learning from each properly or falsely detected or missed allergic reaction event. To automate such machine learning, the present system may include control buttons or other input means allowing to confirm proper allergic events alerts as well as to record when such alerts were generated improperly. For each improperly detected allergic alarm, the system may be configured to adjust (tighten or relax) threshold values for corresponding sensors.

The present invention may be useful for a broad range of allergies, not just caused by food. Other allergies may include medication allergies, environmental allergies, seasonal allergies, contact allergies, etc. In addition, the system of the present invention may be used by more than just children. It may be useful for adults and especially elderly who may have difficulty communicating their condition to the caregiver, for example those with speech impediment or cognitive disorders.

It is contemplated that any embodiment discussed in this specification can be implemented with respect to any method of the invention, and vice versa. It will be also understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, Aft BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12, 15, 20 or 25%.

All of the devices and/or methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An early allergy detection, notification and management system comprising a first watch, said first watch in turn comprising:
   an early allergy detection system comprising at least one ambient sensor, at least one physical activity sensor, and at least one physiological sensor, said at least one physiological sensor is placed on an inner surface of said first watch and configured to detect a symptom of an allergic reaction,
   an early allergy notification system configured to activate a local alarm or a wireless alarm upon detection of an onset of an allergic reaction,
   an early allergy management system comprising a subject locator and a medication storage compartment, and
   a first controller operably connected with said early allergy detection system, said early allergy notification system, and said early allergy management system, said first controller is further configured to detect an onset of an allergic reaction using data from said at least one ambient sensor, said at least one physical activity sensor, and said at least one physiological sensor.

2. The system as in claim 1, wherein said early allergy detection system comprises at least one of an ambient temperature sensor and an ambient humidity sensor.

3. The system as in claim 1, wherein said physical activity sensor comprising a motion detector.

4. The system as in claim 3, wherein said motion detector comprises at least one one-dimension, two-dimension, or three-dimension accelerometer.

5. The system as in claim 3, wherein said at least one physiological sensor is selected from a group consisting of a heart rate sensor, a skin color sensor, a skin galvanic response sensor, an oxygen saturation sensor, a blood pressure sensor, and said motion detector.

6. The system as in claim 5, wherein said blood pressure sensor in turn comprises a wrist sphygmomanometer with an inflatable cuff connected to a pneumatic assembly, said inflatable cuff is located inside a wristband of said first watch so as to facilitate continuous skin contact for remaining sensors of said watch.

7. The system as in claim 5, wherein said first watch comprises a plurality of electrodes positioned on said inner surface thereof, said electrodes are connected to said first controller, wherein said first controller is further configured to use said electrodes for detection of at least a heart rate or a skin galvanic response.

8. The system as in claim 1, wherein said first watch further comprising a GPS receiver.

9. The system as in claim 1 further comprising a wireless beacon, said first controller is further configured to activate said wireless beacon upon detecting an onset of an allergic reaction, whereby affixing said wireless beacon to a medication injector facilitates rapid locating thereof to manage said allergic reaction.

10. The system as in claim 1, wherein said early allergy management system is further configured serve as a medical alert bracelet.

11. The system as in claim 1, wherein said medication storage compartment is waterproof and childproof.

12. The system as in claim 1, wherein said first watch further comprises a first wireless receiver/transmitter.

13. The system as in claim 12 further comprising a second watch, said second watch in turn comprising a second controller operably connected with a second wireless receiver/transducer and at least one of a second motion detector, a second skin color sensor, or a second skin galvanic response sensor.

14. The system as in claim 12 further comprising an additional skin sensor, said skin sensor comprising in turn a third controller operably connected to a third wireless receiver/transmitter and at least one of a third skin color sensor and a third skin galvanic response sensor.

15. A watch-like early allergy detection and notification system comprising:
an early allergy detection system comprising an ambient temperature sensor, a motion detector, and at least one of a heart rate sensor or a skin galvanic response sensor,
an early allergy notification system configured to activate a local alarm or a wireless alarm upon detection of an onset of said early allergic reaction, and
a controller operably connected with said early allergy detection system and said early allergy notification system, said controller is further configured to detect an onset of said early allergic reaction using at least one of the following:
an increase of heart rate above a predetermined heart rate threshold as detected using data from said heart rate sensor;
an onset of skin sweating as detected using data from said skin galvanic response sensor;
an onset of skin itch as detected using data from said motion detector;
said controller is further configured to reduce false alarms by using ambient temperature data from said ambient temperature sensor and physical activity data derived from said motion detector, said ambient temperature and said physical activity data recorded over a predetermined preceding period of time.

16. The system as in claim 15, wherein data from said motion detector is used for both of:
a. determination of extent of physical activity via detection of gross movements of a subject, and
b. detection of skin scratching indicative of an onset of skin itch via detection of repeated periodic movements within a predetermined range of amplitudes and a predetermined range of frequencies.

17. The system as in claim 16, wherein said predetermined range of amplitudes is from about 0.5 inch to about 5 inch.

18. The system as in claim 16, wherein said predetermined range of frequencies is from about 0.5 inch to about 40 times per minute to about 150 times per minute.

19. The system as in claim 16, wherein said skin scratching is detected when a number of such repeated movements in each series of repeated movements is from about 3 to about 20.

* * * * *